US006274872B1

(12) United States Patent
Katerkamp

(10) Patent No.: US 6,274,872 B1
(45) Date of Patent: Aug. 14, 2001

(54) PROCESS AND DEVICE FOR CARRYING OUT QUANTITATIVE, FLUORESCENCE AFFINITY TESTS

(75) Inventor: Andreas Katerkamp, Muenster (DE)

(73) Assignee: ICB Institut fuer Chemo- und Biosensorik Menster E.V. (DE)

(*) Notice: Subject to any disclaimer, the term of this patent is extended or adjusted under 35 U.S.C. 154(b) by 0 days.

(21) Appl. No.: 09/214,566

(22) PCT Filed: Jul. 11, 1997

(86) PCT No.: PCT/DE97/01499

§ 371 Date: May 3, 1999

§ 102(e) Date: May 3, 1999

(87) PCT Pub. No.: WO98/02732

PCT Pub. Date: Jan. 22, 1998

(30) Foreign Application Priority Data

Jul. 11, 1996 (DE) .............................. 196 28 002

(51) Int. Cl.[7] .................................................. G01N 21/64
(52) U.S. Cl. ........................................ 250/458.1; 250/459.1
(58) Field of Search ............................. 250/458.1, 459.1

(56) References Cited

U.S. PATENT DOCUMENTS

| Re. 33,064 | * | 9/1989 | Carter et al. ........................... 436/34 |
| 3,939,350 | | 2/1976 | Kronick et al. . |
| 4,852,967 | * | 8/1989 | Cook et al. ........................ 350/96.29 |
| 4,979,821 | * | 12/1990 | Schutt et al. ......................... 356/246 |
| 5,156,976 | | 10/1992 | Slovacek et al. . |
| 5,192,510 | | 3/1993 | Zoha et al. . |
| 5,194,393 | * | 3/1993 | Hugl et al. ............................. 436/525 |
| 5,350,697 | * | 9/1994 | Swope et al. ......................... 436/527 |
| 5,599,668 | * | 2/1997 | Stimpson et al. ......................... 435/6 |
| 5,766,957 | * | 6/1998 | Robinson et al. .................... 436/165 |
| 5,854,863 | * | 12/1998 | Erb et al. ............................ 250/458.1 |
| 5,919,712 | * | 7/1999 | Herron et al. ........................ 436/518 |
| 5,952,035 | * | 9/1999 | Erb et al. ............................. 427/2.11 |

FOREIGN PATENT DOCUMENTS

WO 89/09408  10/1989 (WO).
WO 90/05295  5/1990 (WO).
WO 90/06503  6/1990 (WO).
WO 94/27137  11/1994 (WO).

OTHER PUBLICATIONS

R.A. Badley et al., "Optical biosensors for immunoassays: the fluorescence capillary–fill device", Phil. Trans. R. Soc. Lund. B 316, pp. 143–160, 1987.

D. Christensen et al., "Analysis of Excitation and Collection Geometries for Planar Waveguide Immunosensors", SPIE vol. 1886 Fiber Optic Sensor in Medical Diagnostics, 1993.

V. Hlady et al., "Spatially Resolved Detection of Antibody–Antigen Reaction on Solid/Liquid Interface using Total Internal Reflection Excited Antigen Fluorescence and Charge–Coupled Device Detection", Biosensors & Bioelectronics, pp. 291–301, 1990.

* cited by examiner

Primary Examiner—Constantine Hannaher
Assistant Examiner—Otilia Gabor
(74) Attorney, Agent, or Firm—Marshall & Melhorn, LLC

(57) ABSTRACT

A process and device are disclosed for carrying out in particular quantitative fluorescence immunity tests by means of evanescent field excitation, possibly on the basis of various known biochemical assays of systems generally composed of receptor-ligands. However, antibody-antigen systems are preferably evaluated. The invention should enable quantitative fluorescence immunity tests with various known biochemical assays to be carried out with a very simple device. For that purpose, a light source is used which emits rays of an almost monochromatic light having a wavelength which causes a marking substance bound to the antibody to become fluorescent. The light rays are directed at an angle α determined by a depth of penetration d previously determined for the evanescent field onto a boundary surface between an optically transparent base plate made of a material with a refraction index $n_1$ is higher than the refraction index $n_2$ of the material above the boundary surface and a cuvette-shaped sample-receiving area. The sample receiving area is covered at the side opposite to the base plate by a covering plate and a detector for sensing fluorescent light is arranged at the same side of the base plate as the light source.

29 Claims, 12 Drawing Sheets

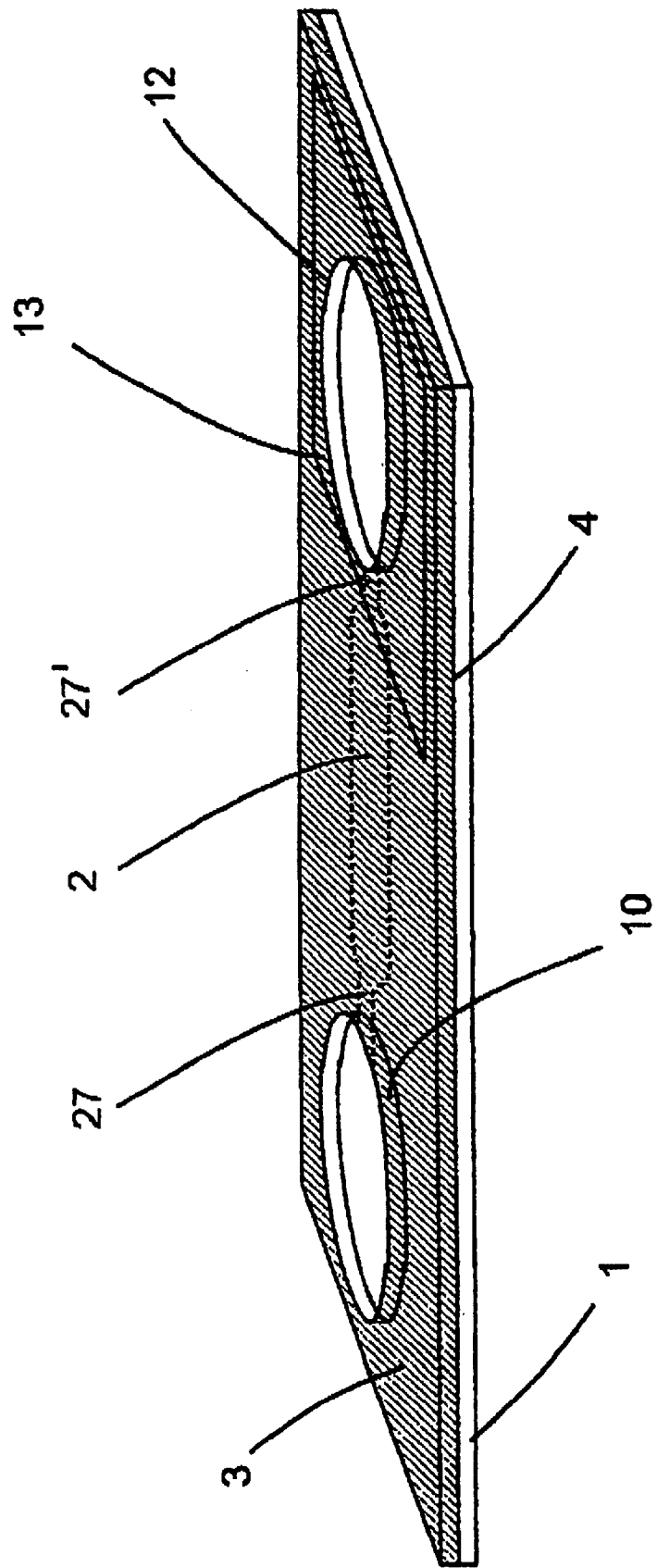

PROCESS AND DEVICE FOR CARRYING OUT QUANTITATIVE, FLUORESCENCE AFFINITY TESTS

BACKGROUND OF THE INVENTION

1. Field of the Invention

The invention relates to a device for carrying out, in particular, quantitative fluorescence-marked affinity tests by means of evanescent field excitation. This may involve a wide variety of known biochemical assays of general receptor/ligand systems, such as antibody/antigen, lectin/carbohydrate, DNA or RNA/complementary nucleic acid, DNA or RNA/protein, hormone receptor, enzyme/enzyme cofactors, [sic] protein or protein A/immunoglobin [sic] or avidin/biotin. Preferably however, antibody/antigen systems are evaluated.

2. Description of the Prior Art

Fluorescence immunotests, or fluorescence immunosensors, use an antibody/antigen system and have long been used widely. They are used primarily to quantify an unknown amount of a particular chemical or biochemical substance in a liquid sample matrix. In this context, antibodies are bound selectively to the substance to be determined. The substance to be determined is referred to by the person skilled in the art as an antigen. In fluorescence immunotests, the analyte-specific antibodies are marked with a marking substance which is optically excited at a particular substance-specific wavelength $\lambda_{ex}$ and the fluorescent light with a different wavelength, which is generally longer, is used with a suitable detector with evaluation of the fluorescent light intensity. The use of evanescent field excitation when implementing such fluorescence immunotests, or respectively the fluorescence immunosensors, already belongs to the prior art. For example, a variety of solutions have already been described in WO 94/27137, by R. A. Badlay, R. A. L. Drake, I. A. Shanks, F. R. S., A. M. Smith and P. R. Stephenson in "Optical biosensors for immunoassays: fluorescence capillary-fill device", Phil. Trans. R. soc. Lund. B 316, 143 to 160 (1987) and D. Christensen, S. Dyer, D. Flowers and J. Herron, "Analysis of Exitation [sic] and Collection Geometries for Planar Waveguide Immunosensors", Proc. SPIE-Int. Soc. Opt. Eng. Vol. 1986, Fiber Optic Sensors in Medical Diagnostics, 2 to 8 (1993). However, the known solutions generally have the disadvantage that they require relatively great outlay in order for the light needed to generate the fluorescence to be coupled into an optical fiber or for the fluorescent light to be extracted, which form an essential part of hitherto customarily used devices.

Further, U.S. Pat. No. 3,939,350 describes a solution in which fluorescence immunoassays are carried out by means of evanescent field excitation.

In this case, light from a light source is directed at an angle through a prism onto an interface, so that total reflection takes place and the fluorescence caused in a sample can be measured with a detector. The entire sample volume is in this case accommodated in a sealed closed space, so that on account of the relatively large sample volume only diffusion-controlled end-point detection can be carried out and this is susceptible to error.

WO 90/05295 describes an optical biosensor system in which [lacuna] an elaborate optical system excitation light can be directed onto sensitive regions of a likewise elaborate channel system, through which the sample volume is fed by means of controlled valves and pumps, and the fluorescent light emerging through windows from the sensitive regions can be re-directed onto a detector with a view to intensity measurement. Besides the aforementioned disadvantageous complex and elaborate structure, this system requires, before and after a test is carried out, cleaning both of the pumps and of the entire channel system in order to preclude the possibility of subsequent measurement errors.

WO 90/06503 describes a sensor in which excitation light is directed at a suitable angle through an optically transparent substrate onto an interface to form an optically transparent buffer layer, over which an extra waveguide layer, to which the analytes to be determined are in turn bound, is applied.

The refractive index of the buffer layer is in this case lower than that of the substrate and of the waveguide. If a suitable choice is made for the angle of the excitation light, total reflection takes place at the substrate/buffer boundary layer [sic] and, by means of the resulting evanescent field, the excitation light is coupled into the waveguide lying over the buffer layer. The light coupled into the waveguide is guided by means of total reflection in the waveguide, and the resulting evanescent field is correspondingly employed for fluorescence excitation.

The sample may be accommodated in one or more cavities, the only restriction on the corresponding dimensioning of such a cavity being that its size permits the sample to be transported into the cavities by means of capillary force. After the sample has been taken in by the cavities, no further flow or movement of the sample takes place.

WO 89/09408 A1 discloses a similar solution, which once more uses the light source for the excitation light and the detector for the fluorescent light on the same side. The sample to be detected is accommodated in a cavity between a waveguide and a cover plate. Here [sic] again no further flow or movement of the sample takes place after the sample has been taken up.

SUMMARY OF THE INVENTION

The object of the invention is therefore to provide the possibility of carrying out quantitative fluorescence-marked affinity tests, with a variety of known biochemical assays, with a very simply constructed device.

According to the invention, this object is achieved by the features in the characterizing part of claim 1 for the device, and the features of claim 25 for the method. Advantageous refinements and developments of the invention result from use of the features contained in the dependent claims.

With the device designed in accordance with the invention, it is possible to carry out fluorescence immunotests in a variety of procedures (assays) and further quantitative fluorescence-marked affinity tests. This provides the opportunity, on the one hand, for carrying out competitive assays, and sandwich assays as well as other known assay forms may further be used.

The procedure adopted when working with the device according to the invention is similar to that already known in the prior art. In this context, a fluorophore is used as marking substance and analyte-specific antibodies are marked using it. The bound fluorophore [lacuna] excited with evanescent field excitation and the fluorescent intensity which this has caused makes it possible to quantify the marked antibodies, and it thus becomes possible to quantify the analyte as well.

In the device according to the invention, light from a light source is directed at an angle $\alpha$ onto the interface between two media with different refractive indices. In this context, a light source is selected which emits almost monochromatic light having a wavelength which is suitable for exciting the marking substance, in this case the fluorophore. Suitable light sources for this include, in particular, laser diodes since they have a suitable beam profile and sufficient optical power, together with a small overall size and low energy consumption.

Other light sources which emit monochromatic light may, however, also be employed.

In this case, care should then be taken that all the optically transparent objects are each transparent to the wavelengths which are used.

The angle α at which the emitted light is delivered to the interface determines, besides the refractive index of the material arranged in the optical path in front of the interface and the material which follows, together with the wavelength of the light, the penetration depth d for the evanescent field. In this case, the refractive index $n_1$ of the material which is arranged in the optical path in front of the interface must permit total reflection at the interface, and should therefore be greater than the refractive index $n_2$ of the other material arranged thereafter, at the wavelengths of the light sources used. The angle α is preferably chosen so as to satisfy: $\sin(\alpha) > n_2/n_1$. If this prerequisite is met, all the light is reflected at the interface and total reflection is therefore achieved. When this condition is met, however, a relatively small part of the light penetrates through the interface into the material which is arranged in the optical path after the interface, and an evanescent field is created. The penetration depth d is defined as corresponding to the distance from the interface at which the intensity of the evanescent field has fallen to the value 1/e, e being equal to the natural logarithm base. The penetration depth d can be calculated using the following equation:

$$d = \frac{\lambda}{2\pi} * \frac{1}{\sqrt{n_1^2 * \sin^2(\alpha) - n_2^2}}$$

With a wavelength λ 700 nm, a refractive index $n_1$=1.51 and a refractive index $n_2$=1.34, if the angle of incidence of the light is α=65° then a penetration depth d of about 400 nm is obtained, and a penetration depth d of about 173 nm is obtained if the angle of incidence α=80°. The consequence of this is that, using the evanescent field, it is only possible to optically excite those marking substances which are in the immediate vicinity of the interface. The result of this, as regards carrying out fluorescence immunotests, is that exclusively the marking substances of the antibodies or antigens which are bound on the surface of the interface are excited. The fluorescent intensity of the light emitted by these fluorophores is therefore directly proportional to the concentration of the marked antibodies bound to the surface and, depending on the biochemical assay used, proportional or inversely proportional to the antigen concentration.

The device designed in accordance with the invention now uses at least one light source which emits almost monochromatic light and directs it onto a baseplate which is transparent to this light at an angle α which predetermines the penetration depth d for the evanescent field. The refractive index $n_1$ of the baseplate should be greater than 1.33. On the other side of the baseplate, a reception region designed in the form of a cuvette is arranged between a cover plate. Between the baseplate and the reception region designed in the form of a cuvette, the aforementioned interface is formed and the evanescent field can act with the predetermined penetration depth d within the reception region in the form of a cuvette on marked chemical or biochemical partners of a receptor/ligand system which are bound to the surface, and excite the fluorophores used as marking substance.

The fluorescence caused by this is measured with the corresponding intensity by a detector. The detector is in this case arranged on the same side of the baseplate as the light source.

The detector used may in this case be an individual photosensitive detector, or a one-dimensional or two-dimensional arrangement of a plurality of photosensitive detectors.

Although, when laser diodes are used, the delivered light is almost monochromatic, a weak broad-spectrum fluorescence background is observed in the laser light. For this reason, a narrow-band excitation filter, which preferably has a spectral bandwidth<10 nm and only transmits light in this narrowly limited wavelength range matched to the light source, is preferably arranged between the light source and the baseplate.

Advantageously, a relatively broadband second filter (emission filter) may also be arranged in front of the detector. This filter prevents light from the light source which is scattered in the material of the baseplate and on reflection at the interface from reaching the detector and vitiating the measurement result. Favorable options for the two filters are the interference filters or edge filters, or a combination of the two.

It is particularly advantageous to direct polarized light onto the sample to be determined. To this end, a polarizer may be arranged in the optical path of the light following on from the light source.

In the case of polarized excitation and detection, it is favorable to make use of the fact that the fluorophores of the marked antibodies, which are firmly bound to the surface, are restricted in their mobility. Consequently, their fluorescent light is oriented in exactly the same polarization plane as the excitation light, and can be detected.

Conversely, the fluorescent light from the fluorophores of the chemical or biochemical substance (antibody), which are not bound to the surface and can consequently move freely, will be oriented in another polarization plane. By using polarized light for the excitation, it is possible to suppress the fluorescent light from the fluorophores bound to the antibodies or antigens, which although lying within the range of the evanescent field are not bound to the surface. The advantage with polarized excitation and detection is apparent if the dimensions of an antibody, about 10 nm, are considered in relation to the penetration depth of the evanescent field, up to about 500 nm. Polarization during excitation and detection, a polarizer also being arranged in front of the detector for this purpose, can improve the ratio of the useful signal to the background signal.

The device designed in accordance with the invention has some essential advantages over those hitherto used.

It has a very simple structure which places little demands on the optical components to be used and, in particular for coupling the light in to excite the fluorophores and/or for extracting the fluorescent light, does not involve any special requirements. Furthermore, a wide variety of biochemical assays can be readily carried out and the essential components can be produced economically, so that even a single use, at least of some parts, is entirely possible. Furthermore, the requisite separation of the chemical components from the sample volume, in relation to the components bound to the surface, is guaranteed.

This is also achieved in that the baseplate and the cover plate, as well as the spacers arranged in between, are made of simple and inexpensively available materials which can be processed using standard technologies. Thus, plastics may be used for the baseplate and cover plate, and a biocompatible adhesive film, which is designed to adhere on both sides, may be used in an advantageous form for the spacer.

The spacer has a thickness of from 0.001 to 10 mm, preferably between 0.001 and 0.5 mm and particularly preferably 50 μm, and by means of a recess forms the reception region for the sample.

The essential basis of the invention is that a defined sample volume is taken through the reception region in the form of a cuvette and subjected there to evanescent field excitation, as described above. The sample volume may in this case be taken through the reception region in the form of a cuvette by suction, pressure [lacuna] capillary forces.

For the binding of a chemical or biochemical component to its complementary chemical or biochemical component fixed on a surface, two physical transport effects must be taken into account in a flowing system, namely convection and diffusion. In this case, the thickness of a diffusive boundary layer (dependent on the flow rate and viscosity) has an essential effect on the binding in terms of quality and rate. If the diffusive physical transport predominates with a relatively thick diffusive boundary layer, rebinding of already bound chemical or biochemical components may take place and vitiate the measurement result. This can be counteracted with the invention by keeping the free cross section of the reception region in the form of a cuvette relatively small, in particular as regards the height. If the flow rate is maintained, this has the cooperative effect that the diffusive boundary layer is negligibly small in the actual detection region. The measurement can thereby be taken substantially faster with satisfactory or, under certain circumstances, even higher accuracy. In many cases, it is even possible to do away with end-point detection, that is to say the entire sample volume does not necessarily have to be taken into account.

In an advantageous embodiment, at least one possible connection, which is at least partly an opening, is provided in a cover plate, and a sample container can be fitted or arranged in it, in this case, the opening is arranged in the cover plate in such a way that a link can be made between the sample container and the reception region. In addition, a second opening is present as a further such possible connection, and is likewise joined to the reception region in the form of a cuvette.

The second opening may likewise be provided in the cover plate. An external pump may be connected to this second opening, or it may have its own pump fitted in it. If it has its own pump, this will preferably consist of a cylindrical hollow body which can be fitted tightly into the second opening. An absorbent material, for example a nonwoven material or paper, is arranged at the bottom of the cylindrical hollow body. The cylindrical hollow body may be closed off with a stopper, a cap or a film. The pumping process is activated by removing the stopper or cap or by making a hole in the film.

The invention may be refined in that a sleeve, which can be closed off at the bottom by a membrane, can be fitted into the aforementioned sample container. In this case, antigens, preferably, may be fixed on the membrane and the requisite marked analyte-specific antibodies needed for carrying out the test may be located on the inner wall of the sleeve.

BRIEF DESCRIPTION OF THE DRAWINGS

The invention will be described in more detail by way of example below.

FIG. 12 shows a further embodiment of a baseplate with a spacer.

DETAILED DESCRIPTION OF THE PREFERRED EMBODIMENTS

Figure 1:
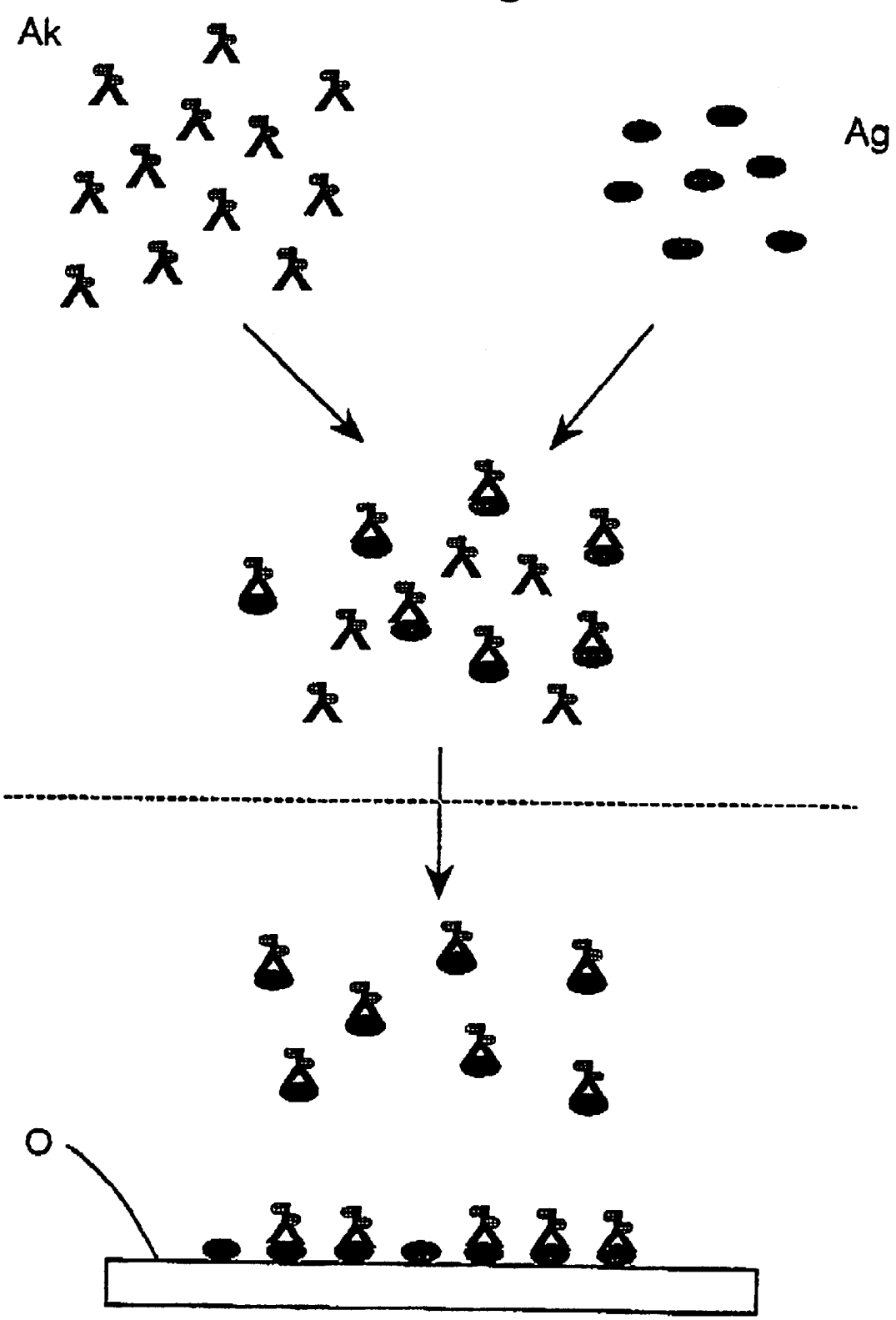
FIG. 1 shows the measurement principle of a competitive assay.

FIG. 1 schematically discloses the measurement principle for carrying out a competitive assay. A known amount of fluorophore-marked analyte-specific antibody Ak is mixed with an unknown amount of antigen Ag to be quantified, the amount of antibody Ak having to be greater than the amount of antigen Ag. The marked analyte-specific antibodies Ak bind to the antigens Ag and, since the amount of marked analyte-specific antibodies Ak is greater than that of the antigens Ag, some marked analyte-specific antibodies Ak remain unbound. The resulting mixture of unbound, or free, marked analyte-specific antibodies Ak is brought into contact with a surface (O) on which the antigen Ag has been fixed. For greater clarity, this phase of the assay is separated by the dashed line in the representation. The still free marked analyte-specific antibodies AK bind to the fixed antigens Ag, while those already bound remain in the solution above the surface. The amount of analyte-specific antibodies Ak which are bound to the surface-fixed antigen Ag is inversely proportional to the antigen concentration which is to be investigated.

The amount of marked analyte-specific antibodies Ak bound to the surface can be quantified by evanescent field excitation and measurement of the fluorescent intensity.

Figure 2:
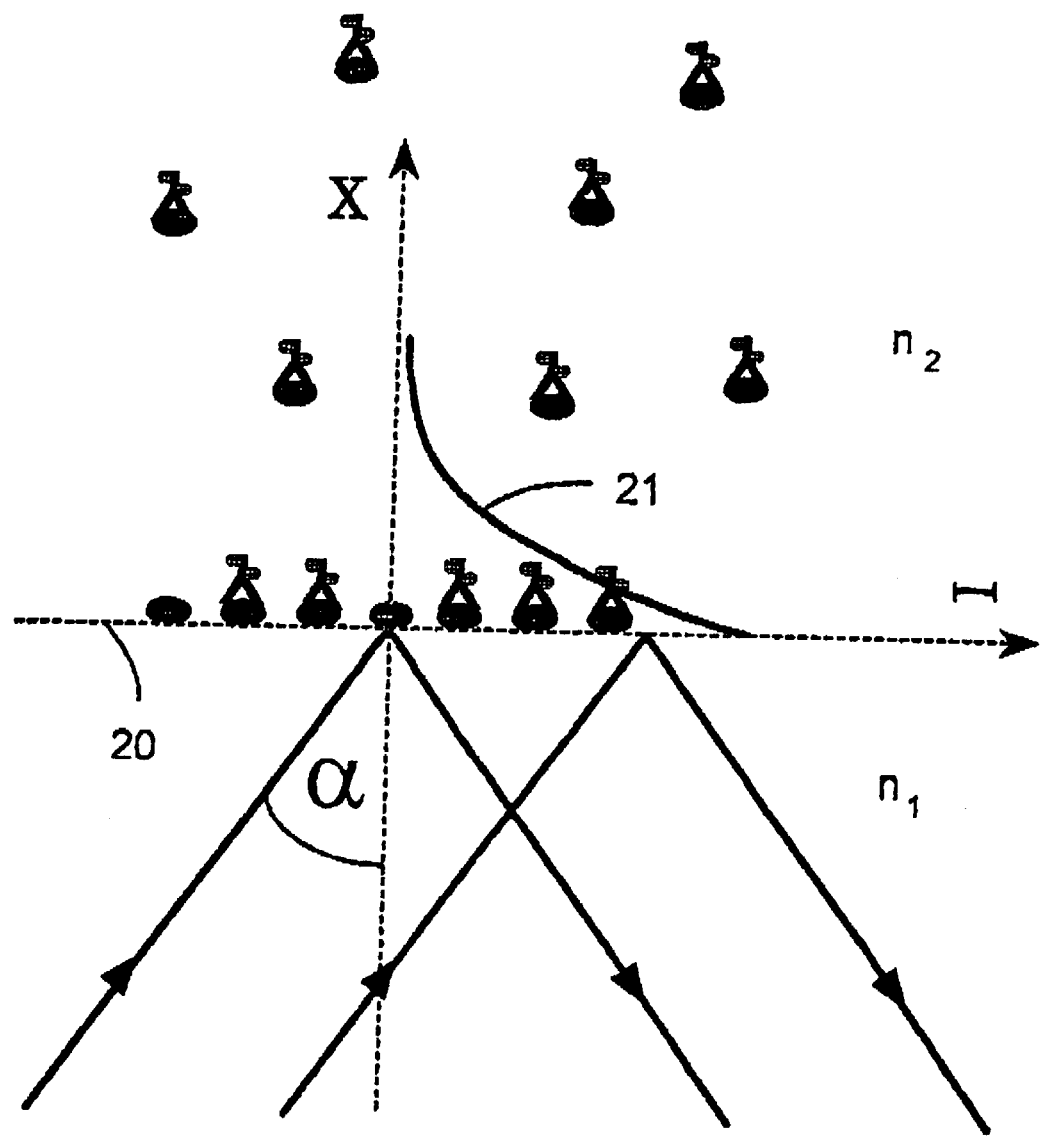
FIG. 2 shows the measurement principle of a fluorescence measurement with evanescent field excitation of surface-bound marked antibodies.

This measurement principle is disclosed by FIG. 2. In this case, light having a wavelength with which the fluorophore as marking substance can be excited is directed at an angle α parallel against the surface which acts as an interface 20 and on which the fixed antigens are bound, through a medium having the refractive index $n_1$ which will subsequently be referred to as the baseplate 1 in the description of FIGS. 5 to 9. The medium having the refractive index $n_1$ is here arranged under the interface 20.

At this surface which serves as an interface 20, total reflection takes place and an evanescent field is formed above this surface, and causes the excitation of the fluorophores.

This being the case, FIG. 2 also represents the intensity I with the curve 21 of the evanescent field as a function of the distance X from the surface acting as the interface 20, it being clear to see that the intensity 21 falls exponentially with increasing distance.

Figure 3:
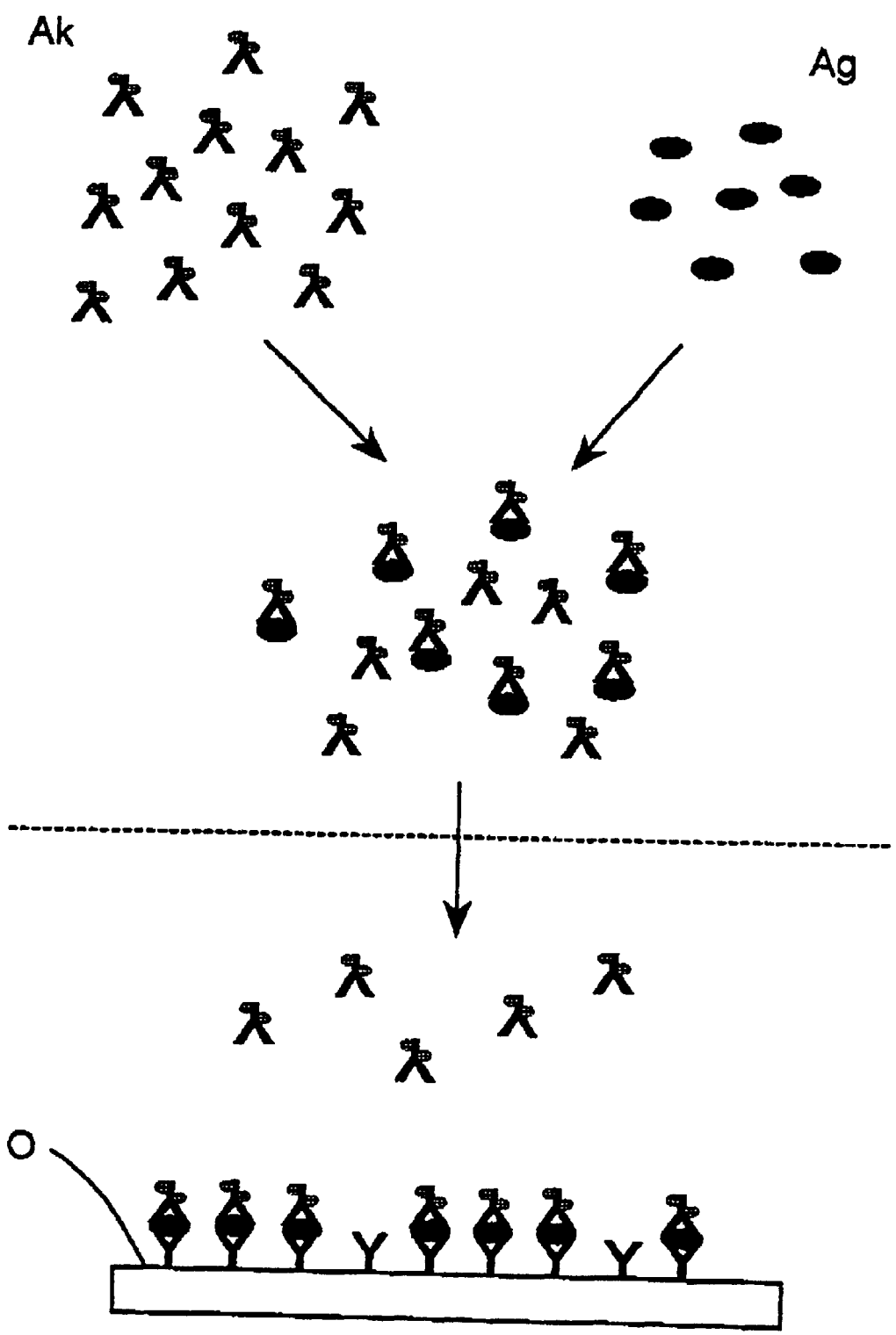
FIG. 3 shows the measurement principle when performing a sandwich assay.

FIG. 3 schematically discloses the procedure of another assay format, a so-called sandwich assay, the phases being once more separated by the dashed line which is drawn. A prerequisite in this case is that there are a pair of analyte-specific antibodies Ak which can both simultaneously bind to the antigen Ag, without these analyte-specific antibodies Ak hindering one another. In this case, one of the two analyte-specific antibodies is marked with a fluorophore. The other of the analyte-specific antibodies Ak is fixed on a surface. After the reaction and surface binding of the second antibody, the fluorophores are then excited with exposure to light of a specific wavelength, and a fluorescence signal is obtained which, in this form of the immunotest, is directly proportional to the antigen concentration. This has the advantage that just a relatively small antigen concentration produces a measurable signal, and even small changes in the antigen concentration can be sensitively registered.

In comparison with this, the competitive assay described above (cf FIG. 1) has the disadvantage that even small antigen concentrations produce a large signal, and small changes can accordingly be measured only with difficulty.

It is generally known that, in sandwich assays, the detection threshold is lower and the sensitivity is higher than with competitive assays. Sandwich assays have the disadvantage with respect to this that there must be a second analyte-specific antibody Ak, and this is only possible if the molar mass of the antigen Ag is substantially in excess of 200 daltons. Antigens with a low molecular weight, for example environmental pollutants, cannot consequently be detected, or can only be detected with difficulty.

It follows from this that competitive assays are universally usable, but have lower sensitivity, whereas, although a sandwich assay is better in these regards, it nevertheless cannot be used in all cases.

Figure 4:
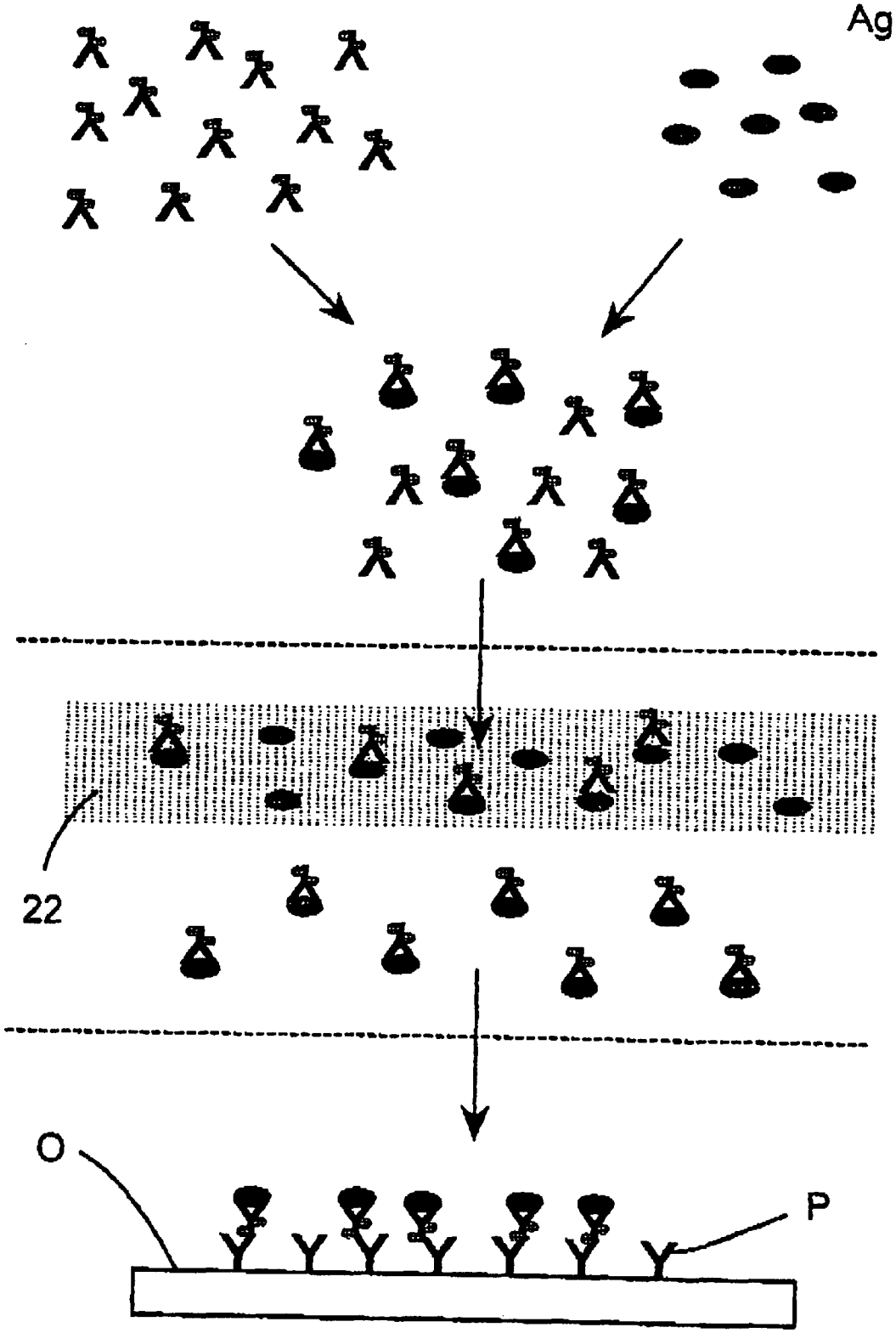
FIG. 4 shows the principle when performing an improved competitive assay.

FIG. 4 describes the principle of a novel assay, for which more detailed explanations, in particular regarding the device to be used, will be given in the description of FIG. 11.

The basis of this novel assay is once more a competitive assay. The mixture of free and bound marked analyte-specific antibodies Ak is fed through a membrane 22, to the surface of which the corresponding antigen Ag is fixed. By way of example, a nitrocellulose membrane may be used as the membrane material. Exclusively the free marked analyte-specific antibodies Ak bind to the antigens Ag fixed there, while those already bound pass through the membrane 22. The liquid following on from the membrane 22 is brought into contact with a surface O on which a protein P is fixed. This protein is capable, independently of the specificity of the marked analyte-specific antibody Ak which is used, of recognizing and binding the latter. The protein P used may, for example, be protein A or an anti-antibody. The fluorescent intensity signal obtained in this assay behaves in accordance with the sandwich assay, and the sensitivity is consequently greater and the possible detection threshold is correspondingly low.

Figure 5:
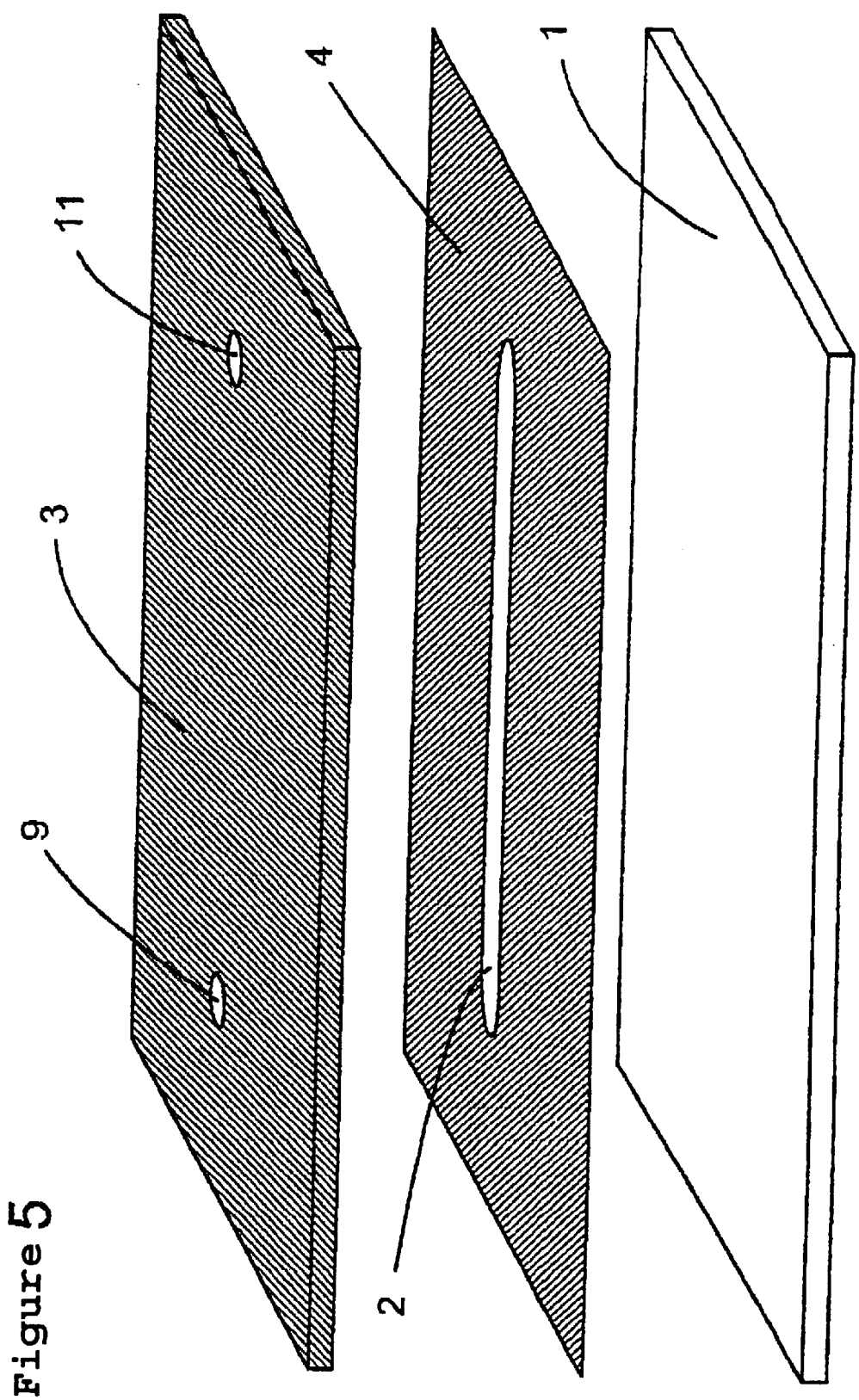
FIG. 5 shows a part of the device according to the invention for a continuous flow arrangement.

FIG. 5 represents the outline structure of a part of the device according to the invention. The three parts illustrated there, the baseplate 1, the spacer 4 and the cover plate 3, may be connected to one another before the fluorescence immunotest is carried out, or may already form a completed unit and be equivalent in their structure to a continuous-flow cell and a measuring cuvette.

In this case, the baseplate 1 is made of a high-index transparent material, for example glass or a plastic, such as a polymer (PMMA or PC) having a refractive index $n_1 > 1.33$. The thickness of the baseplate may lie in a range from 0.01 to 10 mm, preferably between 0.5 and 1 mm.

The spacer 4 is preferably a thin sheet, which is provided on both sides with an adhesive film, or else a thin adhesive film and thus bondable to the baseplate 1, on the one hand, and to the cover plate 3, on the other hand. The total thickness of the spacer, including the adhesive which is used, should lie in a range preferably between 0.001 and 0.5 mm, and quite particularly preferably at a thickness of 50 μm. A hole, which creates a reception region 2 in the form of a cuvette, is made in the spacer 4.

FIG. 5 furthermore shows the cover plate 3 in which through-openings 9 and 11 are formed, in the present example as bores. Their function will be returned to in more detail below. The openings 9 and 11 are in this case arranged in such a way that they at least partly overlap the region of the reception region 2 of the spacer 4. The spacer 4 may preferably be made of a biocompatible adhesive film, which is preferably provided on both sides with a peel-off protection layer and is already commercially available.

Figure 6:
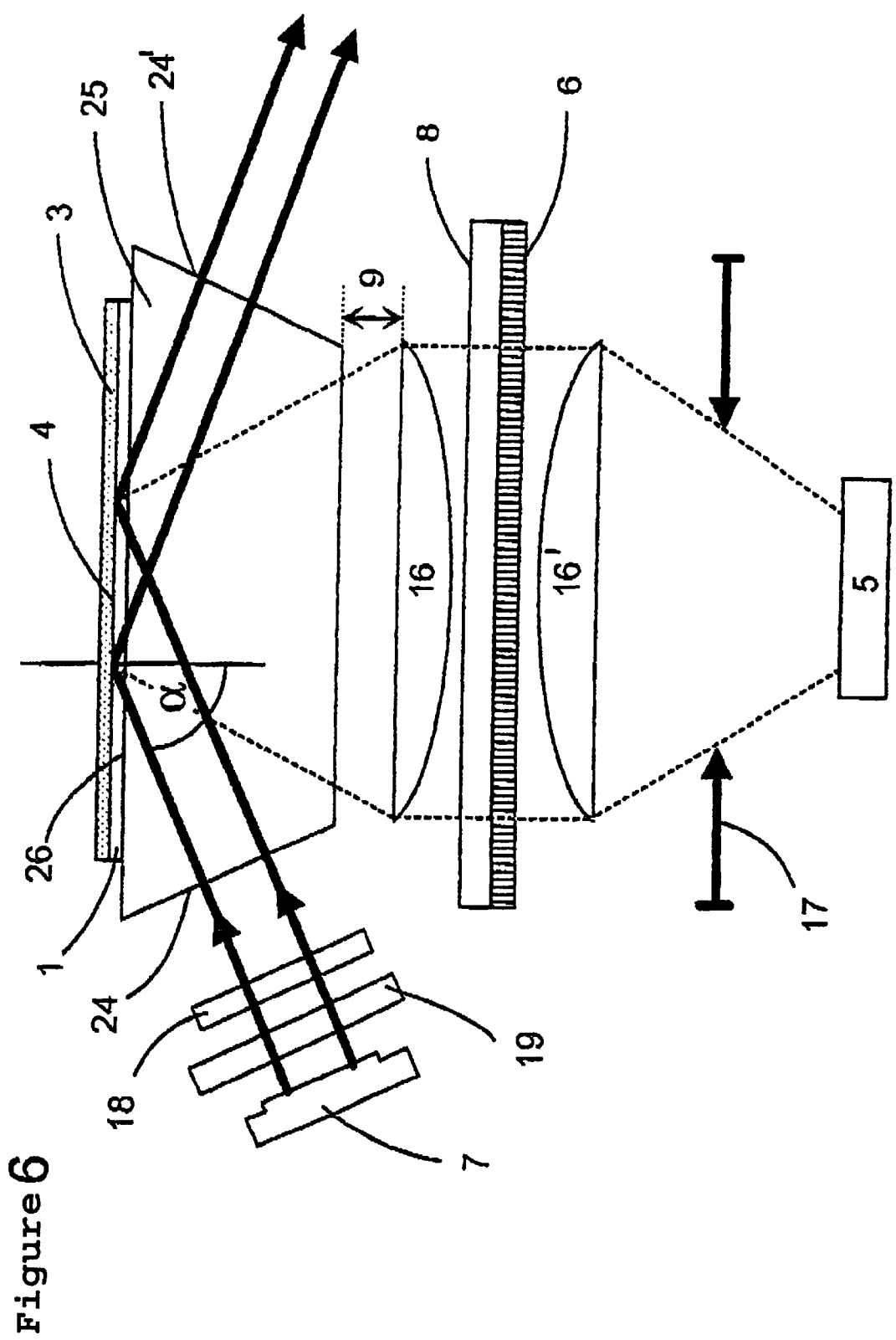
FIG. 6 shows a schematic representation of an embodiment of a device designed in accordance with the invention having a light source.

FIG. 6 shows the outline structure of a device according to the invention. In this case, light from a laser diode 7 is directed through a polarizer 18, through an excitation filter 19, which is of narrow optical band design, onto the reception region 2 formed in the spacer 4 through the baseplate 1. By total reflection at the interface 20 between the baseplate 1 and the reception region 2, evanescent field excitation takes place in the reception region 2 and causes fluorescence of the fluorophores used as marking substance. The fluorescent light passes from there, via a lens 16, through a broadband filter 8, by which the scattered light from the laser diode 7 is kept away from the detector 5. The fluorescent light passes through the downstream polarizer 6 with the aid of the lens 16' onto the detector 5, in front of which a diaphragm 17 is placed. With the detector 5, the fluorescent intensity is picked up and, accordingly, the fluorescence immunotest is carried out and corresponding quantitative determination is made possible.

In the example shown in FIG. 6, the light from the laser diode 7, as described above, is advantageously directed via the polarizer 18 and an excitation filter 19 through an optically transparent body 25 and the baseplate 1 onto the interface 20. Of course, it is also possible for the light to be directed, with omission of the polarizer 18 and excitation filter 19, directly onto an end face 24 of the transparent body 25. The transparent body 25 consists of a material having a refractive index higher than that of the material which is arranged above the interface 20. The transparent body 25 preferably has the same refractive index as the baseplate 1.

Preferably, a body which, for example, is designed as a flattened glass prism or plastic prism, is used as the transparent body 25, in which case a variety of plastics having the said refractive index and other favorable optical properties are to be used.

The transparent body 25 may on the one hand be joined to the baseplate 1 using an adhesive, it being preferable to use an adhesive with the same optical properties. A further possibility consists, in order to obtain optimum optical contact between the high-index optically transparent body 25 and the baseplate 1, to introduce a very thin film 26 (matching fluid) between the two of them, the refractive index of the fluid being the same as the refractive index of the baseplate 1 and the transparent body 25 in the most favorable case. The adhesive or film form [sic] an optical layer 26 for mediating the optical contact between the body 25 and the baseplate 1.

The use of the transparent body 25 has the effect that the majority of the light from the laser diode 7 can reach total reflection at the interface 20 between the baseplate 1 and the reception region 2.

It is in this case particularly favorable to configure and orientate the end face 24 or 24' in such a way that the light from the laser diode 7 impinges orthogonally on this end face 24 or 24', and maximum light yields can thus be coupled in order to achieve total reflection at the interface 20.

In the simplest case, the baseplate 1 and the transparent body 25 may be formed as a common component, so that the join described above, or the use of the very thin film 26 between the transparent body 25 and the baseplate 1, may be omitted.

In this example, use is advantageously also made of a collimator (lens) 16, 16' with which the fluorescent light can be directed concentrated onto the detector 5. In the example shown, the collimator consists of two separate lenses 16 and 16' which are arranged opposite and between which the filter 8 and the polarizer 6 may be located. It is of course also possible for a one-piece lens to be used as the collimator 16.

Figure 8:
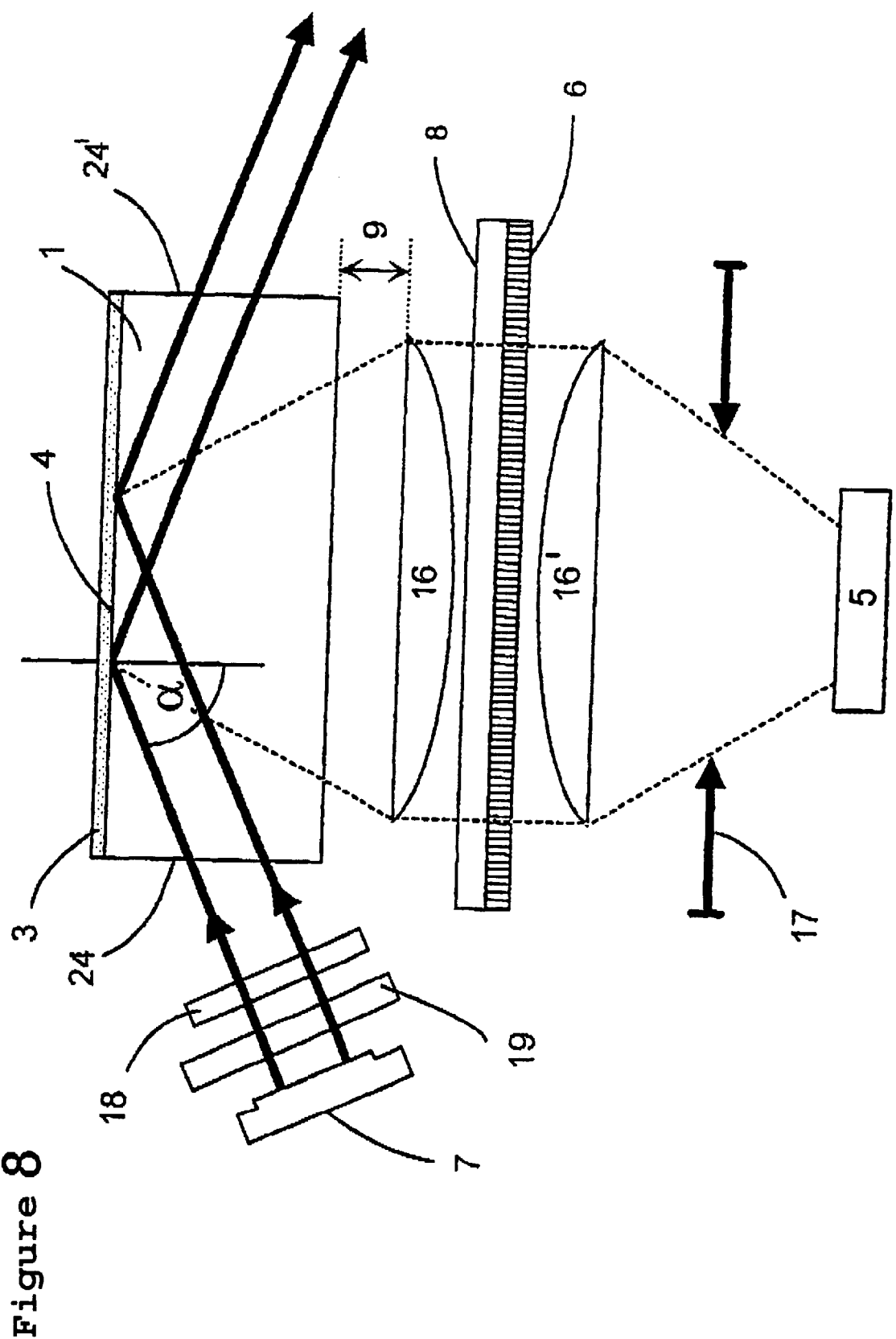
FIG. 8 shows a schematic representation of a further embodiment having one light source.

The distance 9 between the transparent body 25, or the baseplate 1 in the case when it is of one-piece design according to FIG. 8, and the lens 16 should be in the region of between 0 to about 1000 mm.

Figure 7:
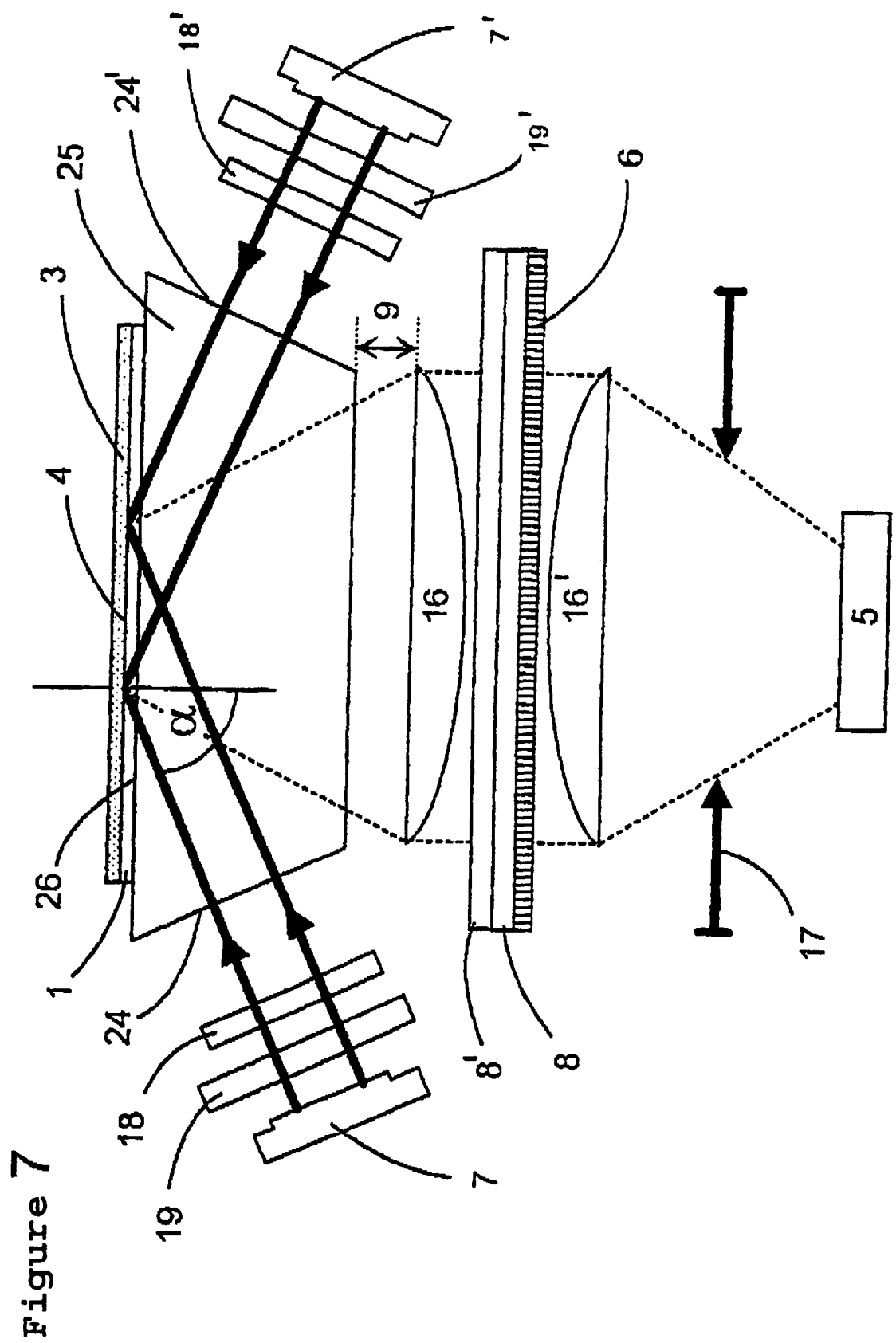
FIG. 7 shows a schematic representation of a second embodiment having two light sources which are used.

The example, represented in FIG. 7, of a device designed in accordance with the invention corresponds essentially to the example which was described above and is shown in FIG. 6. In this case, there are additionally only a second light source 7', a filter 19' and a polarizer 18'. The light source 7' delivers light having a wavelength which differs from the first light source 7. In this example as well, polarized light is preferably used. The device shown in FIG. 7 can advantageously be used when different marking substances, which can be excited at different wavelengths, are used. Examples of this are the fluorophores Cy5 and Cy7. In this case, in order to excite the Cy5 fluorophore, a laser diode having light with a wavelength of between 635 and 655 nm is used, and a laser diode which delivers light having a wavelength of between 730 to 780 nm is used for the Cy7 fluorophore.

In this embodiment, the way in which the measurement is taken is by using either alternately switched diodes 7, 7' or, for example, correspondingly synchronized choppers, so as to ensure that, at any time, only light from one light source 7 or 7' can reach the sample to excite it, and therefore that no spurious results occur.

However, since it is in this case necessary for two different fluorescence signals to be transmitted by the same filter, it is no longer possible to use a broadband filter 8. Two filters 8, 8', which selectively block the wavelengths of the exciting light sources 7, 7' should therefore be arranged one after the other. To this end, for example, notch filters may be used. A further possibility consists in bringing the corresponding filter mechanically into the optical path between the lenses 16 and 16', or removing it therefrom, correspondingly synchronized with the laser diode choppers or the switching on and off. A further possibility consists in leaving the light sources 7, 7' continually switched on and alternately bringing the corresponding filters 8, 8' mechanically into the optical path between the lenses 16, 16' or removing them therefrom.

With this arrangement, on the one hand, it is possible to obtain a reference signal which permits internal calibration of the measurement signal. For the reference measurement, a reference antibody which is not targeted against an antigen from the sample is used. The reference antibody is quantified beforehand and made discriminatable from the analyte-specific antibody Ak to be determined by using a different marking substance. The quantity of reference antibodies actually bound to the surface can be determined using a second light source 7', which causes light of a fluorescence [sic] of different marking substance, a second scattered-light filter 8' and the detector 5. Using this determination, it is possible to account for the losses of marked analyte-specific antibodies Ak or antigens Ag not bound to the surface.

Besides obtaining a reference signal, it is also possible to carry out two immunotests which are run independently of one another, the discrimination being carried out with the aid of the different fluorophores.

Advantageously, a one-dimensional or two-dimensional arrangement of photosensitive detectors may be used as the detector 5. By means of this, it is possible for a plurality of analytes to be detected in a parallel if, depending on the biochemical assay, either different antigens (in the case of a competitive assay) or different analyte-specific antibodies (in the case of a sandwich assay) are fixed in the reception region 2 at different positions, and differently marked analyte-specific antibodies are contained in the sample container 10 in accordance with the amount of different antigens or antibodies. The differently marked analyte-specific antibodies are bound, corresponding to the biochemical assay, at different positions in the reception region 2 and, by focusing the fluorescent light using the collimator 16 onto the one-dimensional or two-dimensional arrangement of a plurality of photosensitive detectors, the fluorescent light is detected with spatial resolution. When only one marking substance is used, for example Cy5, this permits independent parallel quantification of a plurality of analytes from a sample. The detector 5 represented in the figures is then formed by a corresponding arrangement of a plurality of photosensitive detectors.

The illustrative embodiment shown in FIG. 8 corresponds essentially to the example explained above in the description of FIG. 6. In this case, however, the structure has been somewhat simplified in that the baseplate 1 undertakes the tasks of the transparent body 25 and is accordingly of larger design.

The baseplate 1 shown in this example has a rectangular cross section with which, although input coupling losses have to be accepted, the manufacturing cost is reduced. The baseplate 1 may, of course, also be designed as is the case for the transparent body 25 shown in FIG. 6, and the end faces 24 and 24' are inclined in such a way that the light from the laser diode 7 can be orthogonally incident.

Figure 9:
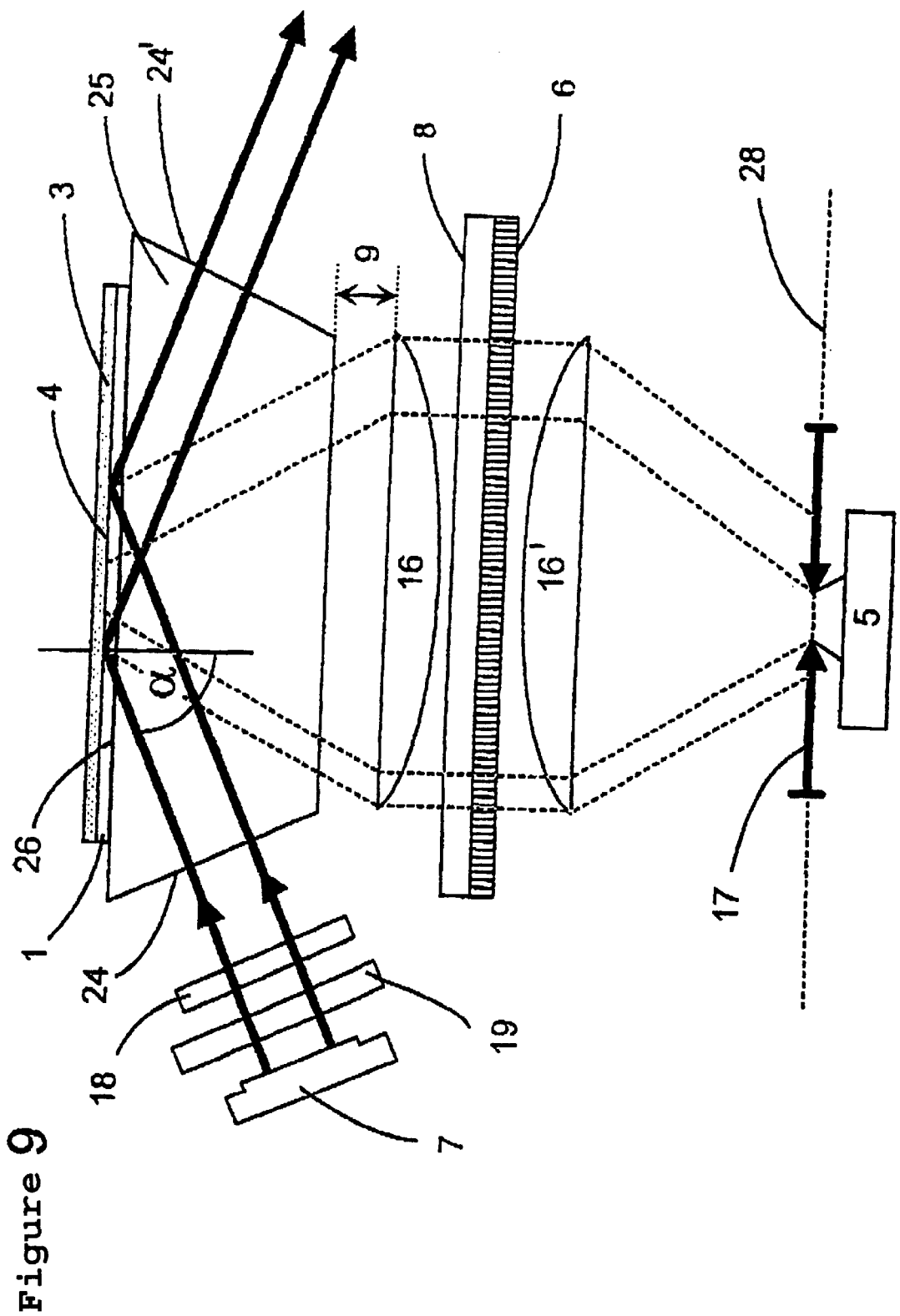
FIG. 9 shows a refined example according to FIG. 6.

FIG. 9 represents a further illustrative embodiment which provides a refinement of the invention. Although the majority of the structure represented has been adopted from the illustrative embodiment shown in FIG. 6, it is also possible for the other embodiments to be supplemented accordingly.

In this example, use is made of a diaphragm 17 which can be moved relative to the detector 5 and the baseplate 1.

The aperture dimensions of the diaphragm 17 may be tailored to the application, so that circular, oval or slit-shaped holes may be used for the diaphragm 17. The size of the free diaphragm cross section may also form a further selection criterion.

For constant free cross section of the diaphragm 17, it may be favorable to configure the diaphragm 17, or the detector 5, in such a way that their mutual separation can be altered. A further possibility consists in providing a rotatable body in which there are a plurality of different diaphragms 17, which differ by size and/or position, so that different regions of the reception region 2 can be imaged and can be acquired with spatial resolution by the detector 5.

Since, when the diaphragm 17 is used, only a fraction of the fluorescent light is focused onto the detector 5, a displaceable diaphragm 17 is represented in FIG. 9.

Preferably, the diaphragm 17 is arranged in the focal plane 28 of the imaging lens system made up of the half-lenses 16 and 16' and arranged in front of the detector 5 in the optical path of the fluorescent light.

By displacing the diaphragm 17, it is possible sequentially to scan the surface of the reception region 2.

When the biochemical assays which have been carried out are ones in which different or identical chemical or biochemical components are fixed at different positions in the reception region 2, and the sample container 10 which is represented contains complementary marked chemical or biochemical substances in accordance with the number of fixed components respectively found there, the binding of the marked complementary substances can be picked up with spatial resolution. This is done by moving the diaphragm 17 parallel and/or orthogonal to the focal plane, the full area of the reception region 2 being comprehensively scanned.

Figure 10:
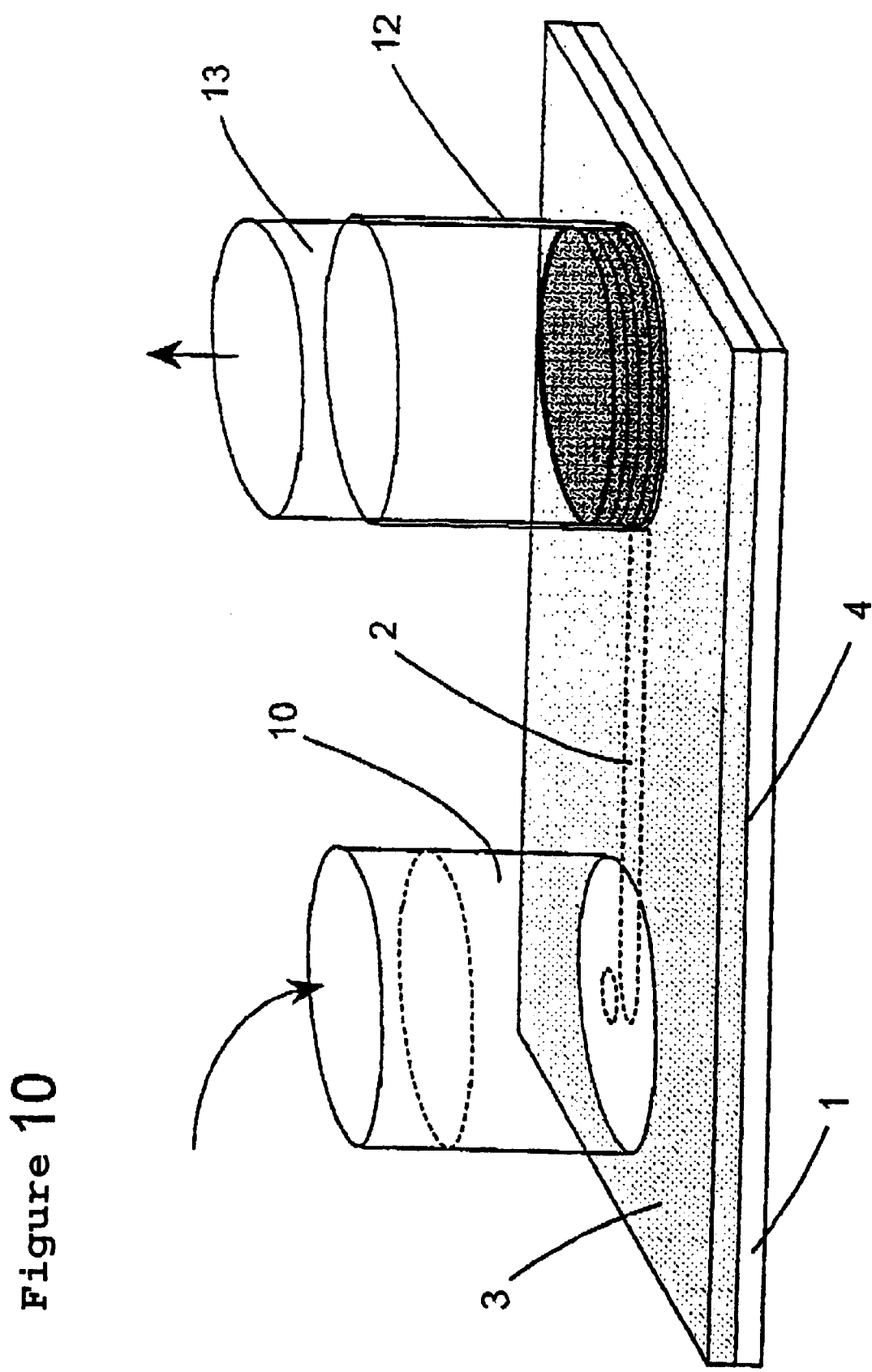
FIG. 10 shows the arrangement of a sample container and a pump in relation to the device according to the invention.

FIG. 10 represents the way in which a sample container 10 is arranged with respect to the opening 9 in the cover plate 3 and a link can thus be made between the sample container 10 through the opening 9 to the reception region 2. In this case, the sample container 10 forms the receptacle in which the known amount of antibodies Ak fluorophore-marked with the marking substance are mixed in with the sample to be determined. The sample container 10 should advantageously always be filled with the same amount, in order to make it possible to obtain reproducible results. It should in this case favorably always be filled to maximum capacity. In all forms of assays which can be carried out, the specific antibody Ak can in each case be located on the surface of the sample container 10 and, through contact with the liquid sample, detached from the surface and passed into the sample. One simple method which is already known consists in applying lyophilized antibodies to the surface of the sample container 10. This makes it possible to store the test for a relatively long time before the immunotest is actually carried out. The reception region 2 defines the area on the baseplate 1 on which, depending on the assay format, the respectively corresponding chemical or biochemical substances are fixed.

FIG. 10 furthermore represents a preferred cylindrical hollow body 12 which accommodates a plunger 13 or another suitable cover (stopper, cap, film), the two of which act together as a pump. If the plunger 13 is moved out from the cylindrical hollow body 12, a vacuum is created which sucks the sample material from the sample container 10 through the reception region 2 in the direction of the cylindrical hollow body 12. Through capillary forces in the reception region 2 and through a liquid-absorbing material, on the bottom of the cylindrical hollow body 12, the flow is sustained until the entire sample volume has been taken through the reception region 2. The cylindrical hollow body 12 is mounted, or has a hole in the bottom, so that there is a link with the reception region 2. This can be achieved by the second opening 11 as a possible connection in the cover plate 3. If no cover plate 3 is used, the possible connection may also be designed in a different way.

It is, however, also possible to connect a separate external pump to the opening 11.

After the sample has been applied, (with the sample container 10), it is necessary to wait a corresponding length of time so that the desired binding between the antigens Ag and the marked antibodies Ak can take place fully. Following this, the pump 12, 13 is activated, and a wait is made until all of the liquid has been pumped through the reception region 2. After excitation with the light source 7, or the light sources 7 and 7', it is then possible to determine the antigen concentration, in which case the structure according to the invention as has been represented in FIGS. 6 and 7 should be employed.

The structure, as has been represented and described above, can be used for a wide variety of biochemical assays.

In competitive assays, analyte-specific antibodies AK marked with a fluorophore are contained unfixed in the sample container 10, and the corresponding antigen Ag is fixed in the reception region 2 on the baseplate 1, which is made of a high-index glass or a polymer or other suitable plastic.

The sample container 10 is then filled with the sample and the analyte binds to the marked antibody Ak. After the reaction, the pump 12, 13 is activated and the marked antibodies which are still free bind to the fixed antigen Ag in the reception region 2 on the baseplate 1. The corresponding amount of marked analyte-specific antibodies Ak can be quantified by measuring the fluorescent intensity, as has been described above.

A further biochemical assay can be carried out as follows. There is a membrane (not shown), on which the antigen Ag is fixed, on the bottom of the sample container 10, and lyophilized analyte-specific antibodies Ak marked with a fluorophore are contained on the walls of the sample container 10. On the surface of the baseplate 1, which is made of a material described above, an anti-antibody or protein A which is targeted against the analyte-specific antibody Ak is, for example, fixed. The sample container is then filled with the sample and the antibodies Ak bind to the analytes. After the reaction, the pump [sic] 12, 13 is [sic] activated and the antibodies Ak which are still free bind to the antigens Ag on the membrane. The analyte-bound antibodies are bound on the surface of the reception region 2, and the corresponding amount can then, as described above, be quantified by using evanescent field excitation.

An important point with all the biochemical assays is for there to be a relatively large sample volume in the sample container 10, all of which is pumped past the small measurement area formed by the reception region 2. Since the height of the reception region 2 is comparatively small, it may be assumed that the corresponding antibodies Ak (free in a competitive assay and bound in a sandwich assay) can reliably reach the surface through the processes of convection and diffusion, and this is actually the case over a large range of flow rates. It is in this way possible to achieve, on the one hand, concentration of the antibodies Ak at the surface and, on the other hand, stable operating reliability so that the process is virtually independent of the through-flow rate.

Figure 11:
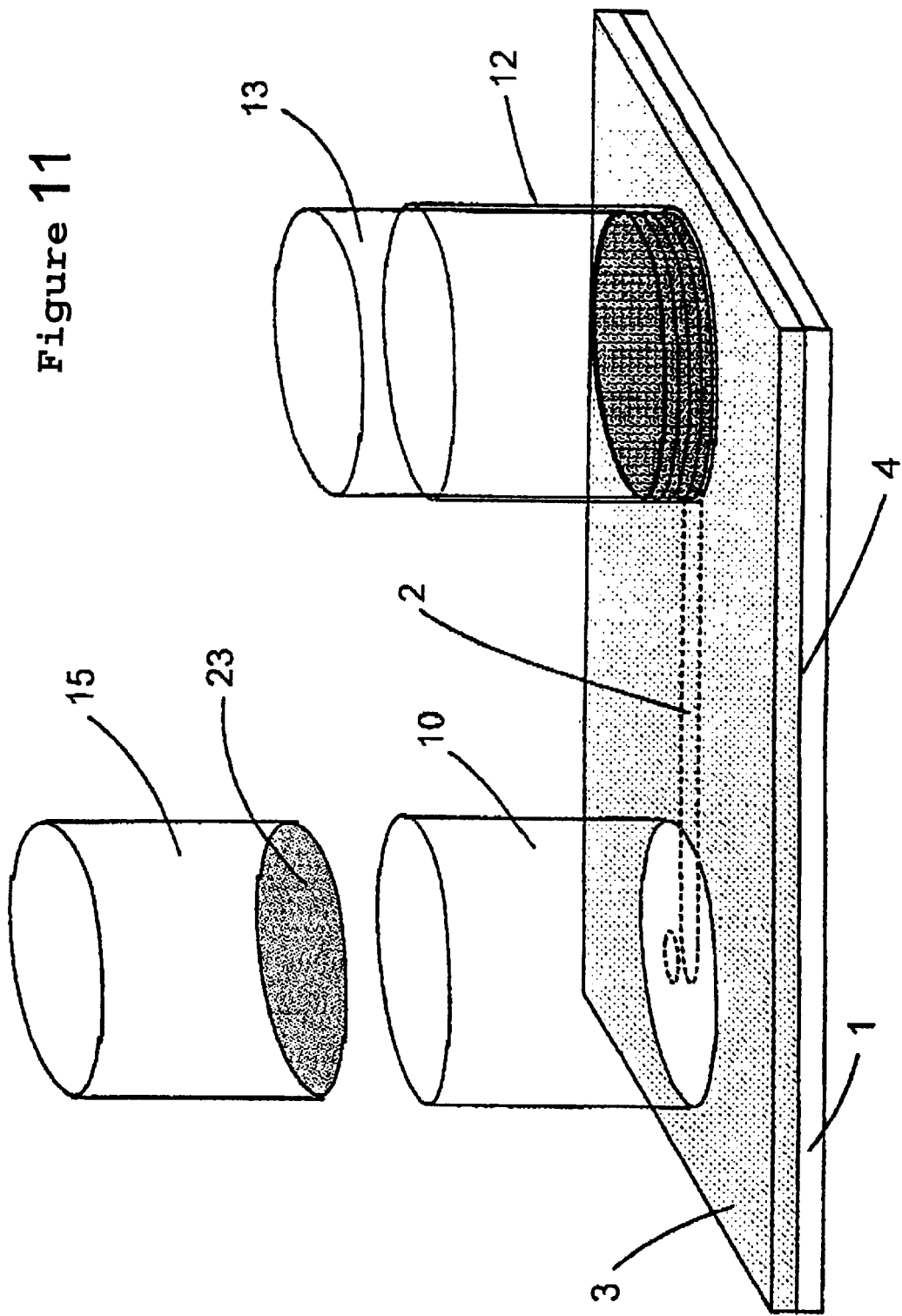
FIG. 11 shows a development of the device according to FIG. 10, with an additionally insertable sleeve.

FIG. 11 gives a further possible illustrative embodiment of the device, with which biochemical assays can be carried out, as was described above in outline in the description of FIG. 4.

In this case, a sleeve 15 which can be pressed into the sample container 10 is additionally used. The sleeve 15 is closed up at the bottom with a membrane 23. On the surface of the inside of the sleeve 15, the lyophilized analyte-specific antibodies and, where appropriate, the reference antibody are contained, and the corresponding antigen is fixed on the surface of the membrane. The assembly can be stored in this condition for a relatively long time. In order to carry out this test according to FIGS. 4 and 9, the device represented in FIG. 7 is preferably used, the different antibodies Ak, or the reference antibody, being marked with different fluorophores. The quantification is then carried out in the manner described above.

In the example shown in FIG. 11, it is again possible for a cylindrical hollow body 12 with fitted plunger 13 to be used, as was described above with reference to the example shown in FIG. 8.

FIG. 12 shows a further refinement of the device according to the invention, in which links 27 and 27', through which the chemical or biochemical substances to be determined can be introduced into the reception region 2 and taken out again, as was described above with reference to the other examples, are formed on both sides of the reception region 2. The spacer 4 shown in FIG. 12 can again be formed in simple fashion by punching, it being possible for everything to be carried out in one punching procedure. In addition, the opening 12 of the cylindrical hollow body 12, which is integrally incorporated in the cover plate 3 and on whose bottom there is again a liquid-absorbing material, or the opening 11 in which there is a liquid-absorbing material, is provided with a film cover 13 which, in the initial condition, hermetically seals the opening 11, or the opening of the cylindrical hollow body 12, and the flow of the sample through the reception region 2 can be initiated simply by breaking the cover sheet 13.

What is claimed is:

1. Device for carrying out quantitative fluorescence-marked affinity tests by means of evanescent field excitation, having at least one light source (7, 7') which emits almost monochromatic light and directs light beams, having a wavelength which causes fluorescence of a marking substance bound to a chemical or biochemical partner of a general receptor/ligand system, at an angle α to be defined by a predeterminable penetration depth d for the evanescent field onto an interface (20) of an optically transparent baseplate (1) made of a material whose refractive index $n_1$ is greater than the refractive index $n_2$ of the material above the interface (20), characterized in that the light is directed through the baseplate (1) onto the interface (20) of a reception region (2) which is in the form of a cuvette and has a thickness of between 0.001 and 0.5 mm, a sample container (10) for receiving the sample is arranged in such a way that a link is formed via a first possible connection (9), which is at least partially an opening between the reception region (2) in the form of a cuvette and the sample container (10) and a second possible connection (11) is linked to the reception region (2) in the form of a cuvette, the reception region (2) being covered on the opposite side from the baseplate (1) with a cover plate (3), and a detector (5) for picking up the fluorescent light being arranged on the same side of the baseplate (1) as the light source (7, 7').

2. Device according to claim 1, characterized in that the baseplate (1) and the cover plate (3) are linked with a spacer (4) in which the reception region (2) in the form of a cuvette is made.

3. Device according to claim 2, characterized in that the spacer (4) is an adhesive film or a sheet.

4. Device according to claim 1, characterized in that the light from the light source(s) (7, 7') can be coupled into the baseplate (1) via at least one end face (24, 24') of the baseplate (1) or an optically transparent body (25) which is linked to the baseplate (1) and is made of a material having a higher refractive index than the material above the interface (20).

5. Device according to claim 4, characterized in that an optically transparent layer (26), whose refractive index corresponds to the refractive index of the baseplate (1) or of the transparent body (25) or the refractive index lies between that of the baseplate (1) and that of the transparent body (25), is formed between the baseplate (1) and the transparent body (25).

6. Device according to claim 1, characterized in that the light source(s) (7, 7') is/are one or more laser diode(s).

7. Device according to claim 1, characterized in that the light source(s) (7, 7') emits/emit polarized light, or a polarizer (18, 18') is arranged behind the light source(s) (7, 7') and a polarizer (6) is arranged in front of the detector (5).

8. Device according to claim 1, characterized in that an optical filter (19, 19') is arranged in the optical path directly behind the or each light source (7, 7').

9. Device according to claim 1, characterized in that at least one optical filter (8, 8') is arranged in front of the detector (5).

10. Device according to claim 1, characterized in that the optical filters (8, 8') can alternately be moved into and out of the optical path between the baseplate (1) and the detector (5).

11. Device according to claim 1, characterized in that chopper(s) is/are arranged in the optical paths.

12. Device according to claim 1, characterized in that the detector (5) is a one-dimensional or two-dimensional arrangement of a plurality of photosensitive detectors.

13. Device according to claim 1, characterized in that at least one lens (16, 16') is/are arranged in the optical path in front of the detector (5).

14. Device according to claim 1, characterized in that a diaphragm (17) is arranged in the optical path between the baseplate (1) and the detector (5).

15. Device according to claim 14, characterized in that the diaphragm (17) can be moved.

16. Device according to claim 1, characterized in that a second light source (7') delivering light having a wavelength which can cause fluorescence of a second marking substance is present, and the light from the two light sources (7, 7') can alternately be directed onto the reception region (2).

17. Device according to claim 1, characterized in that the marking substance(s) is/are fluorophores.

18. Device according to claim 1, characterized in that the baseplate (1) is made of an optically transparent material, such as glass or a plastic.

19. Device according to claim 18, characterized in that use can be made of a hollow body (12) acting as a pump with a cover (13).

20. Device according to claim 19, characterized in that a material (14) which absorbs liquid is arranged in the bottom of the hollow body (12).

21. Device according to claim 1, characterized in that a pump can be connected to or fitted into the second possible connection (11).

22. Device according to claim 1, characterized in that a hollow body (15), on whose inner wall there are antibodies, can be fitted into the sample container (10).

23. Device according to claim 22, characterized in that the hollow body (15) is closed off at the bottom with a membrane (23) on which antigens are fixed.

24. Method for carrying out fluorescence immuno tests by means of evanescent field excitation, characterized in that a sample volume is taken from a sample container (10) through a reception region (2) in the form of a cuvette by suction, pressure or capillary forces and the marked chemical or biochemical components which are to be determined according to the biochemical assay are bound to the corresponding complementary chemical or biochemical components which are fixed on the surface in the reception region (2), and the fluorescent light is measured with a detector (5) by evanescent field excitation by means of the light source (s) (7, 7').

25. Method according to claim 24, characterized in that a reference measurement is carried out with a chemical or biochemical reference component which does not determine an analyte from the sample and which has different marking than the chemical or biochemical component for registering the analyte [lacuna] the amount of chemical or biochemical reference component can be quantified by the second light source (7') and a second optical filter (8') with a detector (5).

26. Method according to claim 24, characterized in that two different marked chemical or biochemical components, bound to different marking substances [lacuna] with two light sources (7, 7') which [lacuna] light with wavelengths that cause fluorescence of the respective marking substance, so that two different analytes from a sample are quantified with the detection of the respective fluorescent intensity.

27. Method according to claim 24, characterized in that, in order to determine the fluorescent intensities of different markings, the beams from the light sources (7, 7') are alternately directed onto the reception region (2) in the form of a cuvette, or the light beams from the light sources (7, 7') are continuously directed onto the reception region (2) in the form of a cuvette and the filters (8, 8') are alternately moved into and out of the optical path between the baseplate (1) and the detector (5).

28. Method according to claim 24, characterized in that different or the same chemical or biochemical components are fixed on the surface in the reception region (2) in the form of a cuvette according to the chosen biochemical assay, at different locations, and complementary chemical or biochemical components are contained in the sample container (10) in accordance with the number of fixed components, the amount of different analytes from the sample being quantified by detecting the different fluorescent intensities of the different locations with a detector (5) made up of one-dimensionally or two-dimensionally arranged photosensitive detectors.

29. Method according to claim 25, characterized in that different or the same chemical or biochemical components are fixed on the surface in the reception region (2) in the form of a cuvette according to the chosen biochemical assay, at different locations, and complementary chemical or biochemical components are contained in the sample container (10) in accordance with the number of fixed components, and the fluorescent intensities of the different locations are picked up with spatial resolution over the entire area of the reception region (2) in the form of a cuvette with the detector (5), by moving a diaphragm (17) whose aperture dimensions are matched to the desired geometrical resolution, and the amount of different analytes from the sample are thereby quantified.

* * * * *